United States Patent [19]

Robertson et al.

[11] Patent Number: 5,279,604
[45] Date of Patent: Jan. 18, 1994

[54] MECHANICAL FASTENING SYSTEMS WITH DISPOSAL MEANS FOR DISPOSABLE ABSORBENT ARTICLES

[75] Inventors: Anthony J. Robertson, Blue Ash, Ohio; Charles L. Scripps, Brookfield, Wis.

[73] Assignee: The Procter & Gamble Company, Cincinnati, Ohio

[21] Appl. No.: 918,156

[22] Filed: Jul. 20, 1992

Related U.S. Application Data

[60] Continuation of Ser. No. 576,316, Aug. 29, 1990, abandoned, which is a division of Ser. No. 134,275, Dec. 17, 1987, Pat. No. 4,963,140.

[51] Int. Cl.⁵ .............................................. A61F 13/15
[52] U.S. Cl. .................................... 604/389; 604/390; 604/391
[58] Field of Search ............... 604/385.1, 385.2, 386, 604/387, 389–392; 128/DIG. 15; 24/442–452

[56] References Cited

U.S. PATENT DOCUMENTS

| | | | |
|---|---|---|---|
| 3,848,594 | 11/1974 | Buell | 604/390 |
| 3,963,029 | 6/1976 | Brooks | 604/390 |
| 4,127,132 | 11/1978 | Karami | 604/390 |
| 4,585,450 | 4/1956 | Rosch et al. | 604/390 |
| 4,699,622 | 10/1987 | Toussant et al. | 604/389 |
| 4,923,455 | 5/1990 | Dean et al. | 604/389 |
| 5,108,384 | 4/1992 | Goulait | 604/390 |

FOREIGN PATENT DOCUMENTS 3176052   7/1991   Japan ...................... 604/385.2

*Primary Examiner*—Randall L. Green
*Assistant Examiner*—K. M. Reichle
*Attorney, Agent, or Firm*—Steven W. Miller; E. Kelly Linman; Jacobus C. Rasser

[57] ABSTRACT

A disposable absorbent article with a mechanical fastening system having an additional fastening element so as to provide convenient disposal of the absorbent article. The mechanical fastening system preferably comprises a tape tab having a first fastening element, a landing member comprising a second fastening element engageable with the first fastening element, and an additional fastening element for allowing the absorbent article to be secured in a configuration that provides convenient disposal of the absorbent article. The additional fastening element preferably comprises a second fastening element affixed to the backing surface of at least one of the tape tabs so that the first fastening element of the opposite tape tab will engage the second fastening element comprising the additional fastening element so as to secure the absorbent article in its disposal configuration.

9 Claims, 4 Drawing Sheets

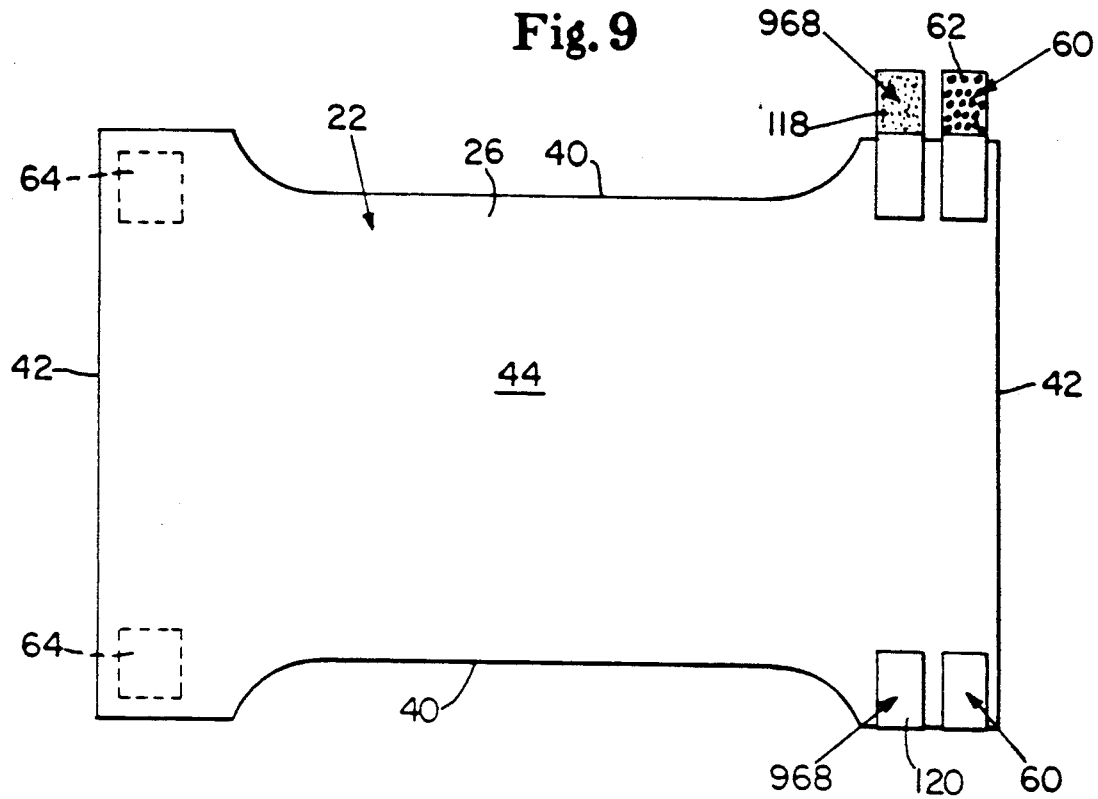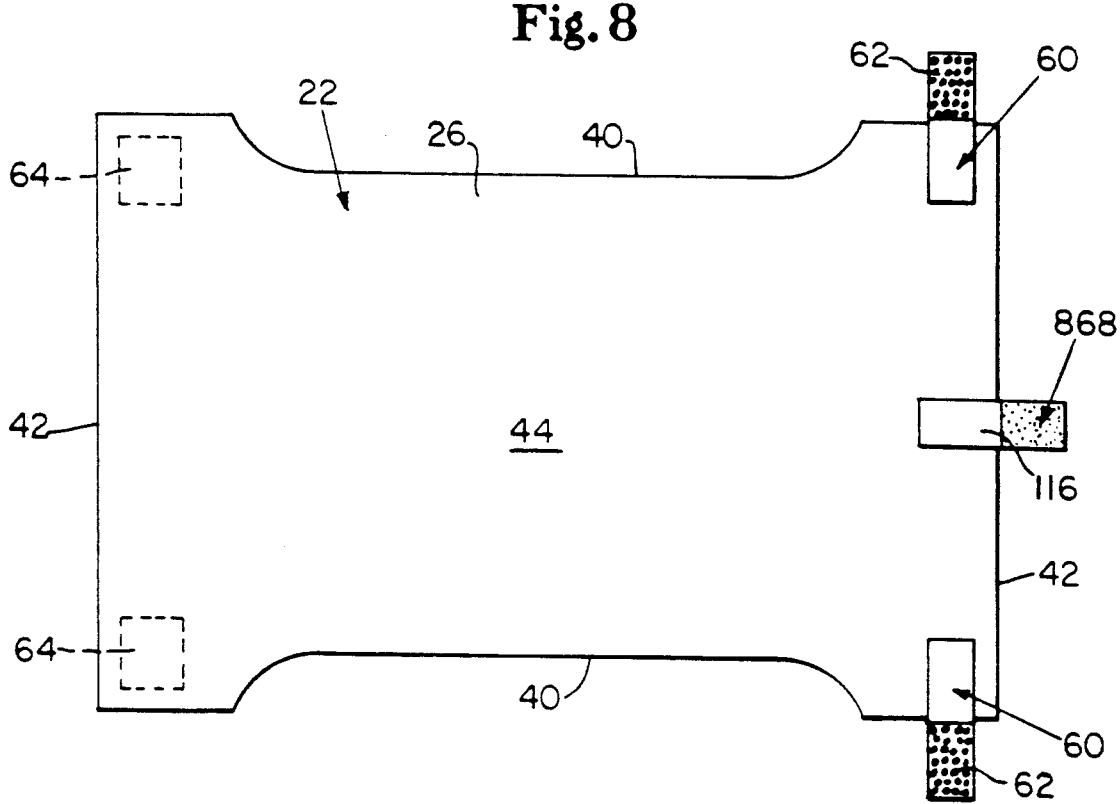

MECHANICAL FASTENING SYSTEMS WITH DISPOSAL MEANS FOR DISPOSABLE ABSORBENT ARTICLES

This is a continuation of application Ser. No. 07/576,316, filed on Aug. 29, 1990, now abandoned which is a divisional of application Ser. No. 07/134,275, filed Dec. 17, 1987, now U.S. Pat. No. 4,963,140.

FIELD OF THE INVENTION

This invention relates to fastening systems for disposable absorbent articles, and more particularly, to an improved mechanical fastening system for such disposable absorbent articles that provides convenient disposal of the absorbent article.

BACKGROUND OF THE INVENTION

The use of adhesive tape fastening systems for securing the corners of a disposable absorbent article such as a diaper is well known in the art. Examples of these types of adhesive tape fastening systems are described in U.S. Pat. No. Re. 26,151 entitled "Disposable Diaper" which issued to Robert C. Duncan et al. on Jan. 31, 1967; and U.S. Pat. No. 3,848,594 entitled "Tape Fastening Systems for Disposable Diaper" issued to Kenneth B. Buell on Nov. 19, 1974.

Adhesive tape fastening systems provide a secure means for keeping a disposable absorbent article on the wearer during use. In addition, refastenable adhesive tape fastening systems allow the disposable absorbent article to be folded or rolled up into a tight package for disposal, secured in the disposal configuration, and easily disposed in waste receptacles. When such adhesive tape fasteners are secured to the rolled-up absorbent article, the contents of the absorbent article are generally prevented from spilling or leaking out while the absorbent article is being thrown away.

Adhesive tape fastening systems have, however, a number of shortcomings, one of which is that they are easily contaminated by oils and powders that come in contact with the adhesive positioned on the tape tabs such that the adhesive does not readily adhere to the absorbent article with sufficient strength to provide an effective side closure. In addition, an adhesive tape fastening system may cause the backsheet of the absorbent article to rip or tear when the fastening system is unfastened to check if the absorbent article has been soiled or to adjust its fit, thereby leaving a hole in the backsheet that renders the fastening system unrefastenable and the absorbent article unuseable. Thus, it would be advantageous to provide a fastening system that is not easily contaminated by oils and powders, that is more convenient to refasten, and that does not render the absorbent article or the fastening system unuseable after unfastening it.

A number of concepts have been proposed for providing washable diapers with mechanical fastening sytems disposed on the body portion of the absorbent article. While mechanical fastening systems, such as hook and loop-type mechanical fasteners, generally provide fastening systems that are not easily contaminated by oils and powders and that are more convenient for refastening than adhesive tape fastening systems, mechanical fastening systems do not provide a disposal mechanism by which the absorbent article may be folded or rolled up into a configuration for disposal, secured in the disposal configuration, and conveniently thrown away. Typically, the hook fastening material is positioned in a first end region of the absorbent article and the loop fastening material is disposed in a second end region of the absorbent article. Thus, when the absorbent article is folded or rolled up for disposal, the loop fastening material is typically tucked underneath other portions of the absorbent article so that the loop fastening material is not exposed such that the hook fastening material, is prevented from engaging the loop fastening material. In addition, because the hook fastening material is incapable of being fastened to the exposed areas of the absorbent article, especially the backsheet, the absorbent article cannot be conveniently secured in a configuration for disposal. Thus, it would be advantageous to provide a mechanical fastening system capable of providing convenient disposal of the absorbent article.

It is, therefore, an object of the present invention to provide a disposable absorbent article having an improved fastening system.

It is a further object of the present invention to provide a disposable absorbent article having an improved mechanical fastening system.

It is an additional object of the present invention to provide a disposable absorbent article having a mechanical fastening system provided with disposal means to provide convenient disposal of the disposable absorbent article.

These and other objects of the present invention will be more readily apparent when considered in reference to the following description and when taken in connection with the accompanying drawings.

SUMMARY OF THE INVENTION

According to the present invention, a disposable absorbent article such as a diaper is provided with a mechanical fastening system having disposal means so as to provide convenient disposal of the absorbent article.

While the mechanical fastening system may take many forms, it preferably comprises a closure member comprising a tape tab and a first fastening element, a landing member comprising a second fastening element engageable with the first fastening element of the closure member, and disposal means. In use, the first fastening element engages the second fastening element to provide a secure side closure for the absorbent article. After the absorbent article has been soiled, it is folded or rolled up into a configuration for disposal that generally prevents the contents of the soiled absorbent article from spilling or leaking out of the absorbent article. The absorbent article is then secured in its disposal configuration by the disposal means.

The disposal means of the present invention may comprise any means wherein the absorbent article may be secured in a disposal configuration so as to contain the contents of the soiled diaper. Thus, the disposal means may comprise a number of different elements positioned on either the body portion or the fastening system of the absorbent article. Preferably, the disposal means comprises a second fastening element affixed to the backing surface of at least one of the tape tabs so that the first fastening element of the opposite tape tab will engage the second fastening element of the disposal means so as to secure the absorbent article in its disposal configuration. Thus, the disposal means may comprise a mechanical fastening element such as a hook fastening material or a loop fastening material that is positioned on the tape tab. Alternatively, the disposal means may comprise any other mechanical fastening element, an adhesive attachment means disposed on the body portion or the fastening system, or a separate adhesive tape tab or tape tabs positioned on the body portion for use when the absorbent article has been soiled.

BRIEF DESCRIPTION OF THE DRAWINGS

FIG. 8 is a top plan view of a diaper embodiment incorporating another alternative embodiment of the present invention.

FIG. 9 is a top plan view of a diaper embodiment incorporating a still further alternative embodiment of the present invention.

DETAILED DESCRIPTION OF THE INVENTION

Mechanical fastening systems of the present invention are useful and beneficial when applied to disposable absorbent articles. As used herein, the term "disposable absorbent article" refers to articles which absorb and contain body exudates and, more specifically, refers to articles which are placed against or in proximity to the body of the wearere to absorb and contain the various exudates discharged from the body and which are intended to be discarded after a single use (i.e., they are not intended to e laundered or otherwise restored or reused). A preferred embodiment of the disposable absorbent article of the present invention is a diaper 20. As used herein, the term "diaper" refers to a garment generally worn by infants or incontinent persons that is drawn up between the legs and fastened about the waist of the wearer. Examples of the kinds of diapers to which the present invention is very readily adapted are shown in the above-referenced U.S. Pat. No. 26,151, issued to Duncan et al. and in U.S. Pat. No. 3,860,003 entitled "Contractable Side Portions for Disposable Diaper" which issued to Kenneth B. Buell on Jan. 14, 1975, both of which are incorporated herein by reference. It will be apparent from the following description that the mechanical fastening system illustrated and described herein may be applied to the body portion of such diapers. On the other hand, it will be understood that the invention is not limited to any specific diaper structure or configuration.

Figure 1:
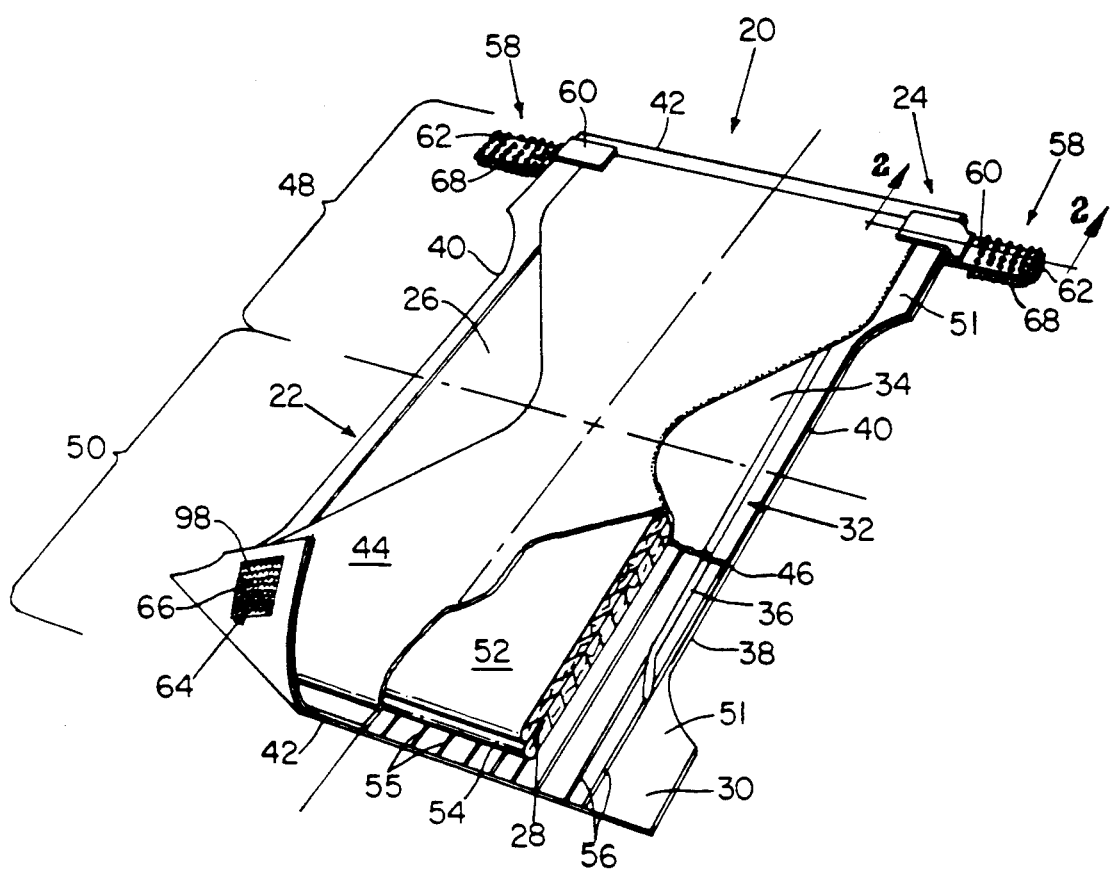
FIG. 1 is a partially cut-away perspective view of a diaper embodiment incorporating the present invention.

Referring to the drawings, it will be noted that FIG. 1 is a partially cut-away perspective view of the diaper 20 of the present invention prior to its being placed on the diaper wearer by the diaper user. As can be seen in FIG. 1, a preferred diaper 20 comprises a body portion 22 and a fastening system 24. A preferred body portion 22 comprises a liquid pervious topsheet 26, an absorbent core 28, a liquid impervious backsheet 30, and elastically contractible leg cuffs 32 comprising a side flap 34 and one or more elastic members 36. While the topsheet 26, the absorbent core 28, the backsheet 30, the side flaps 34 and the elastic members 36 may be assembled in a variety of well known configurations, a preferred disposable diaper configuration is shown and described generally in the above-referenced U.S. Pat. No. 3,860,003 which issued to Kenneth B. Buell on Jan. 14, 1975, and which patent is incorporated herein by reference.

FIG. 1 shows a preferred embodiment of the body portion 22 in which the topsheet 26 and the backsheet 30 are coextensive and have length and width dimensions generally larger than those of the absorbent core 28. The topsheet 26 is superposed on the backsheet 30 thereby forming the periphery 38 of the body portion 22. The periphery 38 defines the outer perimeter or, in other words, the outer extent of the body portion 22. The periphery 38 comprises longitudinal edges 40 and end edges 42.

The body portion 22 has an inside surface 44 and an outside surface 46. In general, the outside surface 46 of the diaper 20 extends from one end edge 42 to the other end edge 42 of the diaper and from one longitudinal edge 40 to the other longitudinal edge 40 of the diaper and is the surface farthest from the wearer during use of the diaper 20. When a backsheet 30 is used, it typically forms the outside surface 46 of the body portion 22. The inside surface 44 is that surface of the diaper opposite the outside surface 46 and in the embodiment shown in typically formed by the topsheet 26. In general, the inside surface 44 of the diaper 20 is that surface coextensive with the outside surface 46 and which is for the greater part in contact with the wearer when the diaper 20 is worn.

The diaper 20 has first and second end regions 48 and 50, respectively, extending from the end edges 42 of the diaper periphery 38 toward the lateral centerline of the diaper 20. Both the first end region 48 and the second end region 50 extend a distance of about one-half of the length of the diaper 20 such that the end regions comprise each half of the diaper 20.

Both the first end region 48 and the second end region 50 have panels 51. The panels 51 are those portions of the first end region 48 and the second end region 50 which overlap when the diaper 20 is fastened about the waist of the wearer. The extent to which the end regions overlap and thus the extent to which the panels 51 are formed will depend on the overall dimensions and shape of the diaper 20 and the size the wearer.

The absorbent core 28 of the body portion 22 may be any means which is generally compressible, conformable, non-irritating to the wearer's skin, and capable of absorbing and retaining liquids and certain body exudats. The absorbent core 28 may be manufactured in a wide variety of sizes and shapes (e.g., rectangular, hourglass, asymmetric, etc.) and from a wide variety of liquid absorbent materials commonly used in diapers and other disposable absorbent articles, such as comminuted wood pulp which is generally referred to as the airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent core 28 should, however, be compatible with the design exudate loading in the intended use of the diaper 20. Further, the size and absorbent capacity of the absorbent core 28 may be varied to accommodate wearers ranging from infants to adults.

While the absorbent core 28 may comprise a single layer of absorbent material such as the configuration described in U.S. Pat. No. 4,610,678 entitled "High-Density Absorbent Structure" which issued to Paul T. Weisman and Steven A. Goldman on Sep. 9, 1986 and which patent is incorporated herein by reference, a preferred embodiment of the absorbent core 28 is a dual-layered absorbent core in a preferred configuration such as is generally described in U.S. Pat. No. 4,673,402 entitled "Absorbent Article With Dual-Layered Cores" which issued to Paul T. Weisman, Dawn I. Houghton and Dale A. Gellert on Jun. 16, 1987, and which is incorporated herein by reference, having an asymmetric-shaped upper layer 52 and a lower layer 54. The upper layer 52 preferably acts as a liquid acquisition/distribution layer comprised primarily of hydrophilic fiber material. The lower layer 54 acts as a fluid storage layer comprised of a mixture of hydrophilic fiber material and particles of an absorbent gelling material (hydrogel material. Both the upper layer 52 and the lower layer 54 preferably comprise an absorbent layer encased in a tissue layer. It should be understood, however, that the size, shape, configuration, and total absorbent capacity of the upper layer 52 or the lower layer 54 may be varied to accommodate wearer's ranging from infants through adults. Therefore, the dimensions, shape, and configuration of both the upper layer 52 and the lower layer 54 may be varied (e.g., the upper layer or the lower layer may have a varying caliper, a hydrophilic gradient, a rapid acquisition zone or may contain absorbent gelling material).

The absorbent core 28 is superposed on the backsheet 30 and is preferably associated thereto by a core attachment means 55 such as those well known in the art, for example , pressure-sensitive adhesives, hot melt adhesives or other adhesives; ultrasonic bonding; or heat/pressure sealing. The absorbent core 28 may be secured to the backsheet 30 by a uniform continuous layer of adhesive, a patterned layer of adhesive, or any array of separate lines or spots of adhesive. An adhesive which has been found to be satisfactory is preferably a hot-melt adhesive such as manufactured by Eastman Chemical Products Company of Kingsport, Tenn. and marketed under the tradename of Eastobond A-3 or by Century Adhesives, Inc., of Columbus, Ohio and marketed under the tradename Century 5227. The core attachment means 55 preferably comprise an open pattern network of filament of adhesive as is shown in U.S. Pat. No. 4,573,986 entitled "Disposable Waste-Containment Garment" which issued to James A. Minetola and David R. Tucker on Mar. 4, 1986, and which is incorporated herein by reference.

The backsheet 30 is impervious to liquids and is preferably manufactured from a thin plastic film, although other flexible liquid impervious materials may also be used. The backsheet 30 prevents the exudates absorbed and contained in the absorbent core 28 from soiling articles which contact the diaper 20 such as bedsheets and undergarments. Preferably, the backsheet 30 is a polyethylene film having a thickness of from about 0.012 mm (0.5 mil) to about 0.051 mm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 30 is preferably embossed and/or matte finished to provide a more clothlike appearance. Further, the backsheet 30 may permit vapors to escape from the absorbent core 28 while still preventing exudates from passing through the backsheet 30.

The size of the backsheet 30 is dictated by the size of the absorbent core 28 and the exact diaper design selected. In a preferred embodiment, the backsheet 30 has a modified hourglass shape extending beyond the absorbent core a minimum distance of at least about 1.3 cm to about 2.5 cm (about 0.5 to about 1.0 inch) around the entire diaper periphery 38.

the topsheet 26 of the body portion 22 of the present invention is compliant, soft feeling, and non-irritating to the wearer's skin. Further, the topsheet 26 is liquid pervious permitting liquids to readily penetrate through its thickness. A suitable topsheet 26 may be manufactured from a wide range of materials such as porous foams, reticulated foams, apertured films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from liquids retained in the absorbent core 28.

A particularly preferred topsheet 26 comprises staple length polypropylene fibers having a denier of about 1.5, such as Hercules Type 151 polypropylene fibers marketed by Hercules, Inc. of Wilmington, Del. As used herein, the term "staple length fibers" refer to those fibers having a length of at least about 15.9 mm (0.625 inches).

There are a number of manufacturing techniques which may be used to manufacture the topsheet 26. For example, the topsheet 26 may be woven, non-woven, spunbonded, carded, hydroformed or the like. A preferred topsheet 26 is carded and thermally bonded by means well known to those skilled in the fabric art. Preferably, the topsheet 26 has a basis weight from about 15 to about 30 grams per square meter, a minimum dry tensile strength of at least about 400 grams per centimeter in the machine direction and a wet tensile strength of at least about 55 grams per centimeter in the cross-machine direction.

The topsheet 26 and the backsheet 30 are associated together in any suitable manner as is well known in the diaper manufacturing art. As used herein, the term "associated" encompasses configurations whereby the topsheet 26 is directly joined to the backsheet 30 by affixing the topsheet 26 directly to the backsheet 30, and configurations whereby the topsheet 26 is indirectly joined to the backsheet 30 by affixing the topsheet 26 to intermediate members which in turn are affixed to the backsheet 30. In a preferred embodiment, the topsheet 26 and the backsheet 30 are joined directly to each other in the diaper periphery 38 by a flap attachment means 56 such as an adhesive or any other attachment means as is known in the art. In general, the core attachment means 55 that affixes the absorbent core 28 to the backsheet 30 is the same means as the flap attachment means 56 that affixes the topsheet 26 to the backsheet 30. Thus, for example, a uniform continuous layer of adhesive, a patterned layer of adhesive, an array of separate lines or spots of adhesive, or a network of adhesive filaments such as shown in the above-referenced U.S. Pat. No. 4,573,986 may be used.

Elastically contractible leg cuffs 32 are disposed adjacent the periphery 38 of the body portion 22, preferably along each longitudinal edge 40, so that the leg cuffs 32 tend to draw and hold the diaper 20 against the legs of the wearer. While the leg cuffs 32 may comprise any of several means as are well known in the diaper art, a particularly preferred leg cuff construction comprises a side flap 34 and one or more elastic members 36, as is described in detail in the hereinbefore referenced U.S. Pat. No. 3,860,003. In addition, a method and apparatus suitable for manufacturing a disposable diaper having elastically contractible leg cuffs are described in U.S. Pat. No. 4,081,301 entitled "Method and Apparatus For Continuously Attaching Discrete, Stretched Elastic Strands to Predetermined Isolated Portions of Disposable Absorbent Articles" which issued to Kenneth B. Buell on Mar. 28, 1978, and which patent is incorporated herein by reference. In a preferred embodiment, the elastically contractible leg cuff 32 comprises a side flap 34 and an elastic member 36 comprising an elastic thread.

The diaper 20 is provided with a fastening system 24 for forming a side closure. Thus, the diaper 20 is fitted to the wearer and the first end region 48 and the second end region 50 are maintained in an overlapping configuration when the diaper 20 is worn.

In a preferred embodiment of the present invention as shown in FIG. 1, the fastening system 24 comprises a closure member 58, preferably comprising a tape tab 60 and a first fastening element 62, disposed adjacent each longitudinal edge 40 of the body portion 22 in the first end region 48; a landing member 64, preferably comprising a second fastening element 66 engageable with the first fastening element 62, disposed on the outside surface 46 of the body portion 22 in the second end region 50; and disposal means 68 positioned on either the body portion 22 or the fastening system 24, preferably on the tape tab 60, for allowing the diaper 20 to be secured in a disposal configuration so as to provide convenient disposal of the diaper 20.

Each closure member 58 is intended to provide a mechanical fastening means for engaging a landing member 64 so as to provide a secure side closure for the diaper 20. Thus, the closure member 58 comprises at least a first fastening element 62. Each closure member 58 also preferably comprises a means for positioning the first fastening element 62 adjacent the landing member 64 so as to achieve a side closure. Thus, the closure member 58 may comprise any of the well known configurations and securement means for achieving a side closure on a diaper such as an inner fastening member secured to the inside surface and/or the outside surface of the body portion, tape tabs, or belts. Preferred closure members 58 for the diaper 20 comprise either an inner fastening member or a tape tab.

An inner fastening member comprises a fastening element or a combination of fastening elements such as a first fastening element and adhesive attachment means positioned on the body portion 22 of the diaper 20. Thus, a preferred inner fastening member consists of a first fastening element comprising a strip or a patch of a hook fastening material. While an inner fastening member may be positioned anywhere on the body portion such as on the inside surface 44 or the outside surface 46, or in the first end region 48 or the second end region 50; an inner fastening member is preferably positioned on the inside surface 44 of the body portion 22 in the panels 51 in the first end region 48, one adjacent each longitudinal edge 40, so as to engage a landing member 64. The first fastening element of each inner fastening member is joined to the body portion and preferably covers an area about 1 inch wide (i.e., generally perpendicular to longitudinal centerline) by about 2.5 inches long (i.e., generally parallel to the longitudinal centerline) at the panels 51 of the body portion 22. An exemplary embodiment of an inner fastening member is described in U.S. Pat. No. 4,699,622 entitled "Disposable Diaper Having an Improved Side Closure" issued to John W. Toussant and Margaret H. Hasse on Oct. 13, 1987, which is incorporated herein by reference.

Figure 2:
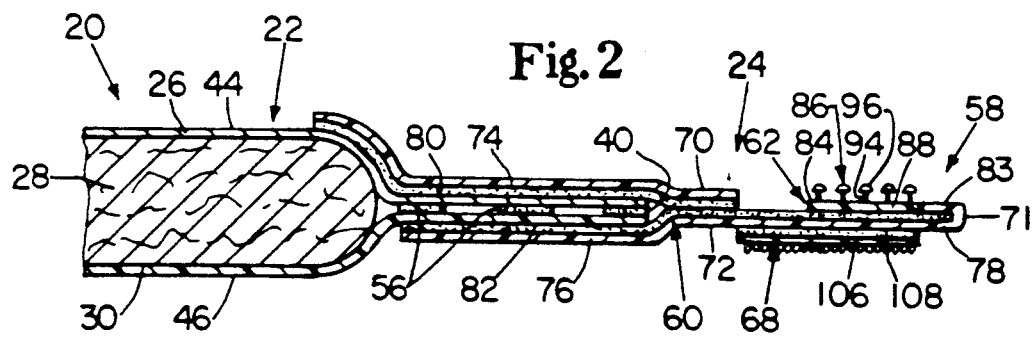
FIG. 2 is a cross-sectional view of the corner of the diaper taken along line 2—2 of FIG. 1.

As shown in FIGS. 1 and 2, the closure member 58 most preferably comprises a tape tab 60. Any of the well known configurations and constructions of a tape tab may be used. A preferred tape tab 60 is a Y-shaped tape tab as described in detail in U.S. Pat. No. 3,848,594 entitled "Tape Fastening System for Disposable Diaper" which issued to Kenneth B. Buell on Nov. 19, 1974, and which patent is incorporated herein by reference. Alternatively preferred tape tabs are described in detail in co-pending U.S. continuation patent application Ser. No. 078,345 entitled "Disposable Diaper Having Wide Tapered Fastening Tapes" filed Jul. 28, 1987 by Harold R. Burkhardt and Kenneth B. Buell, which is incorporated herein by reference. As shown in FIG. 1, a tape tab 60 is provided on both longitudinal edges 40 of the body portion 22, most preferably in the first waist region 48.

A particularly preferred tape tab 60 is illustrated in FIG. 2 and has a fastening surface 70 and a backing surface 72. The fastening surface 70 is that surface of the tape tab 60 designed to engage the landing member 64 of the present invention. Thus, the fastening surface 70 of the tape tab 60 will generally correspond to the inside surface 44 of the body portion 22. The backing surface 72 is that surface opposite of the fastening surface 70 and generally corresponds to the outside surface 46 of the body portion 22. The backing surface 72 is thus generally exposed during wear of the diaper 20.

The preferred tape tab 60 illustrated in FIG. 2 is one which is anchored to both the inside surface 44 and the outside surface 46 of the body portion 22 to create a manufacturer's end (i.e., that attachment of the tape tab 60 to the diaper 20 made during manufacture of the diaper 20). The tape tab 60 has another element which forms the user's end (i.e., that joint made by the person in securing the diaper to the wearer). Thus, the preferred tape tab 60 of the present invention has at least three elements, a first fixed portion 74, a second fixed portion 76, and a connective portion 78. The first fixed portion 74 is that portion of the tape tab 60 which is attached to the inside surface 44 of the body portion 22. The second fixed portion 76 is that portion of the tape tab 60 which is attached to the outside surface 46 of the body portion 22. The first fixed portion 74 and the second fixed portion 76 thus form the manufacturer's end of the tape tab 60. The connective portion 78 is that portion of the tape tab 60 which is attached to another portion of the diaper 20, generally the landing member 64, by the user when securing the diaper 20 on the wearer. The connective portion 78 thus forms the user's end. Additionally, the outer surface of the second fixed portion 76 and the outer surface of the connective portion 78 form the backing surface 72 of the tape tab 60 while the inner surface of the first fixed portion 74 and the inner surface of the connective portion 78 form the fastening surface 70 of the tape tab 60.

The preferred Y-shaped tape tab 60 of the present invention can be constructed in several ways. The first fixed portion 74, the second fixed portion 76, and the connective portion 78 can each be separate tapes which meet and are joined adjacent the longitudinal edge 40 of the body portion 22 in an area of joinder. A more practical structure for the tape tab 60 is one in which the connective portion 78 and either the first fixed portion 74 or the second fixed portion 76 are a unitary strip of tape material. If the connective portion 78 is unitary with the second fixed portion 76 as shown in FIG. 2, then the first fixed portion 72 is a separate element which is attached to the combined connective portion and the second fixed portion adjacent to the longitudinal edge 40 of the body portion 22.

FIG. 2 also shows tab attachment means for securing the tape tab 60 to the body portion 22. These tab attachment means are any of those attachment means which provide an adequate bond, and preferably are any of the pressure-sensitive adhesives well-known to those of ordinary skill in the adhesive art. The outer surface of the first fixed portion 74 is affixed to the inside surface 44 of the body portion 22 by a first tab attachment means 80. The inner surface of the second fixed portion 76 is affixed to the outside surface 46 of the body portion 22 by a second tab attachment means 82. The connective portion 78 is provided with a first fastening element 62 joined to it preferably by the second tab attachment means 82 (alternatively, a third tab attachment means if the connective portion 78 is a separate element from the second fixed portion 76), although an adhesive attachment means may be placed on the first fastening element 62 separately and the combined material joined to the connective portion 78.

Preferred materials for the tape tabs 60 comprises a tape material such as tape code numbers XPF 14.43.0, Y-9376, or Y-9030 available from The Minnesota Mining and Manufacturing Company, St. Paul, Minn. The tape material in the embodiments are preferably a polyethylene film having a tab attachment means tailored to bond to the polyethylene positioned on the tape material. The tape tab attachment means may comprise any of those adhesives which provide an adequate bond with other portions of the diaper, and is preferably any of the pressure-sensitive adhesives well-known to those of ordinary skill in the art. Preferred tab attachment means is a pressure-sensitive adhesive such as code number XPF 1.42.34 available from The Minnesota Mining and Manufacturing Company, St. Paul, Minn.

As shown in FIG. 2, the tape tab 60 may also have a grip tab 83 at the distal edge 71 in the connective portion 78. The grip tab 83 may be formed by folding over a small margin of the distal edge 71 of the connective portion 78 and attaching it to itself. This forms an end on the connective portion 78 which is easier to grasp by the diaper user when the diaper 20 is to be fitted and attached to the wearer. The grip tab 83 is most beneficial when used when the connective portion 78 is superposed on the first fixed portion 74.

The first fastening element 62 of the closure member 58 forms the closure between the closure member 58 and the landing member 64. Thus, the first fastening element 62 provides an element or elements that engage the second fastening element 66 of the landing member 64 to maintain the first end region 48 and the second end region 50 in an overlapping configuration to provide a secure side closure. The first fastening element 62 may thus comprise any of the well known means for achieving a closure such as buttons, snaps, hook fastening materials, or loop fastening materials.

The first fastening element 62 may be a separate member joined to and associated with the closure member 58 or a unitary member with the closure member 58. For example, the topsheet 26 may be manufactured so as to mechanically engage the landing member 64 (the topsheet 26 being a unitary first fastening element 62), or a discrete patch or strip of material may be joined with the body portion 22 or the tape tab 60 (a separate first fastening element 62). Preferably, the first fastening element 62 is a separate material joined to the fastening surface 70 of the tape tab 60.

The first fastening element 62 is preferably joined to either the body portion 22 or the tape tab 60. As used herein, the term "joined" encompasses configurations whereby the first fastening element 62 is releasably secured to the diaper 20 so that the first fastening element 62 may be removed from the diaper 20 or its location during sue and whereby the first fastening element 62 is affixed to the diaper 20 such that the first fastening element 62 is securely fastened to the diaper 20. Joined is also used to denote that the first fastening element 62 may be directly joined to the diaper 20 or may be indirectly joined to the diaper 20 such as by releasably securing or affixing the first fastening element 62 to an intermediate member which in turn is releasably secured or affixed to the diaper 20. Preferably, as shown in FIG. 2, the first fastening element 62 is directly affixed to the connective portion 78 of the tape tab 60 by the second tab attachment means 82.

The first fastening element 62 may be positioned anywhere on the diaper 20. When the closure member 58 comprises an inner fastening member, the first fastening element 62 is preferably positioned in the panels 51 of the first end region 48 adjacent the longitudinal edges 40. When the closure member 58 comprises a tape tab 60, the first fastening element 62 is preferably positioned either on all of or at least a portion of the fastening surface 70, more preferably on all of or at least a portion of the connective portion 78. Most preferably, the first fastening element 62 is disposed on a first area (a portion) of the connective portion 78 on the fastening surface 70 and adjacent the distal edge 71 of the tape tab 60. An exemplary embodiment of this configuration is discussed in C. Locke Scripps' co-pending U.S. patent application, now U.S. Pat. No. 5,019,065, entitled "Disposable Absorbent Article With Combination Mechanical And Adhesive Tape Fastener System", which is incorporated herein by reference.

FIG. 2 shows a preferred first fastening element 62 of the present invention. The first fastening element 62 of the present invention preferably comprises a hook fastening material 84. As used herein, the term "hook fastening material" is used to designate a material having engaging elements 86. Thus, the hook fastening material 84 may also be referred to as a male fastener. It should also be understood that the use of the term "hook" should be non-limiting in the sense that the engaging elements 86 may comprise any shapes as are known in the art so long as they are adapted to engage a complementary second fastening element 66. As shown, the hook fastening material 84 preferably comprises a base 88 having a first surface and a second surface and a plurality of engaging elements 86 extending from the first surface of the base 88. Each of the engaging elements 86 are shown to comprise a stem 94 supported at one end on the first surface of the base 88 and an enlarged head 96 positioned at the end of the stem 94 opposite of the base 88.

The preferred hook fastening material 84 of the present invention is intended to engage fibrous elements of a loop fastening material so as to provide a secure fastening device. Thus, the hook fastening material 84 may be manufactured from a wide range of materials. Suitable materials include nylon, polyester, polypropylene, or any combination of these materials. A suitable hook fastening material 84 comprises a number of shaped engaging elements 86 projecting from a woven backing such as the commercially available material designated "Scotchmate" brand No. FJ3402 available from Minnesota Mining and Manufacturing Company, St. Paul, Minn. Alternatively, the engaging elements may have any shape such as hooks, "T's" or any other shape as are well known in the art. A particularly preferred hook fastening material is described in C. Locke Scripps' co-pending U.S. patent application Ser. No. 07/007,841 entitled "Disposable Diaper Having An Improved Fastening Device" filed Jan. 26, 1987, and which is incorporated herein by reference.

The landing member 64 of the fastening system 24 provides a means for securing itself and the closure member 58 together to provide a secure side closure and to maintain the first end region 48 and the second end region 50 in an overlapping configuration. The landing member 64 may be disposed anywhere on the diaper 20 so long as it engages the closure member 58 so as to provide the side closure. For example, the landing member 64 may be disposed on the outside surface 46 in the second end region 50, on the inside surface 44 in the first end region 48, or on any other portion of the diaper 20 which is disposed to engage the closure member 58. In addition, the landing member 64 may either be a discrete separate element affixed to the diaper 20 or a unitary piece of material that is neither divided nor discontinuous with an element of the diaper 20 such as the topsheet 26 or the backsheet 30. While the landing member 64 can assume varying sizes and shapes, it preferably comprises one or more separate patches of material secured to the body portion 22 to allow for a maximum fit adjustment at the waist of the wearer. The preferred embodiment of the diaper 20 illustrated in FIGS. 1 and 5 has an elongated, rectangular-shaped landing member 64 secured to the outside surface 46 of the body portion 22 in the panels 51 of the second end region 50 adjacent each of the longitudinal edges 40.

The landing member 64 preferably comprises a second fastening element 66 engageable with the first fastening element 62 of the closure member 58. Thus, the second fastening element 66 may be manufactured from a wide range of materials and configurations capable of securely engaging the first fastening element 62. For example, the second fastening element 66 may comprise identical complementary elements with the first fastening element 62 or distinct complementary elements with the first fastening element 62. As used herein, the term "identical complementary elements" is used to define mechanical fastening systems wherein the engaging elements of the first fastening element 62 and the second fastening element 66 comprise the same configuration or structure that are interlocking. Examples of such systems are described in U.S. Pat. No. 4,322,875 entitled "Two Strip Materials Used For Forming Fasteners" issued to Brown et al. on Apr. 16, 1982 and U.S. Pat. No. 4,701,179 entitled "Fixed Position Fasteners For Disposable Absorbent Garments" issued to Kellenberger et al. on Oct. 20, 1987. The term "distinct complementary elements" is used herein to designate a system wherein the first fastening element 62 is different from the second fastening element 66 but is engageable therewith such as buttons and holes, a hook fastening material and a loop fastening material, or a male member and a female member. Preferably, the second fastening element 66 comprises a hook fastening material or a loop fastening material depending upon whether the first fastening element 62 is a loop fastening material or a hook fastening material. As shown in FIG. 1, the landing member 64 preferably comprises a second fastening element 66 comprising a plurality of fiber elements such as a loop fastening material 98.

The loop fastening material 98 of the second fastening element 66 provides a plurality of fiber elements that engage the engaging elements 86 of the hook fastening material 84. The loop fastening material 98 may be manufactured from a wide range of materials to provide fiber elements, preferably loops. Such suitable materials include nylon, polyester, polypropylene, or any combination of these materials. A suitable loop fastening material 98 comprises a number of fiber loops projecting from a woven backing such as the commercially available material designated "Scotchmate" brand nylon woven loop No. SJ3401 available from Minnesota Mining and Manufacturing Company, St. Paul, Minn. A preferred loop fastening material 98 comprises a tricot knit fabric having a plurality of nylon filament loops projecting from a backing of nylon such as the commercially available material designated "Guilford No. 16110" available from Guilford Mills of Greensboro, N.C. Alternatively, the loop fastening material 98 may be a non-woven fabric or any other type of fiber material or loop material which are well known in the art. An inexpensive loop fastening material and a method of making such a loop fastening material is described in U.S. patent application Ser. No. 040,520, entitled "Loop Fastening Material For Fastening Device And Method Of Making Same" filed Apr. 24, 1987, by C. Locke Scripps and J. Richard Noel, which application is incorporated herein by reference.

The disposal means 68 of the present invention provides a component that allows convenient and easy disposal of the diaper 20. Thus, the disposal means 68 may be any structure that allows the diaper 20 to be folded or rolled up into a configuration for disposal and secured in that configuration to contain the contents within the soiled diaper. Thus, for example, the disposal means 68 may comprise a number of different elements positioned on either the body portion 22 or the fastening system 24 such as adhesive tape tabs, adhesive attachment means, mechanical fastening elements, a hook fastening material, a loop fastening material, a first fastening element and a second fastening element, or any other element or combination of elements readily known to those of skill in the art.

The disposal means 68 may be positioned anywhere on either the body portion 22 or the fastening system 24 of the diaper 20 so long as it secures the diaper 20 in a configuration for disposal. For example, the disposal means 68 may be positioned on the inside surface 44 of the body portion 22, on the outside surface 46 of the body portion 22, in the first end region 48 or in the second end region 50, or on the fastening system 24 such as on an element of one or both of the tape tabs 60. The disposal means 68 may be positioned on the fastening surface 70 or the backing surface 72 of the tape tab 60, on the connective portion 78, the first fixed portion 74, the second fixed portion 76 or any combination of the elements of either or both of the tape tabs 60.

In addition, the disposal means 68 may be either a discrete separate element joined to the diaper 20 or a unitary element that is a single piece of material that is neither divided nor discontinuous with an element of the diaper 20 such as the topsheet 26, the backsheet 28, or one of the first fastening elements 62. (For example, one of the first fastening elements may comprise a disposal means if the fastening material is an identical complementary element since the first fastening element of one tape tab may be secured to the first fastening element of the other tape tab.) While the disposal means 68 may be a number of different elements and can assume varying sizes and shapes, preferred disposal means 68 comprise either an adhesive tape tab or a mechanical fastening element such as a second fastening element positioned to allow for disposal of the diaper 20.

Figure 5:
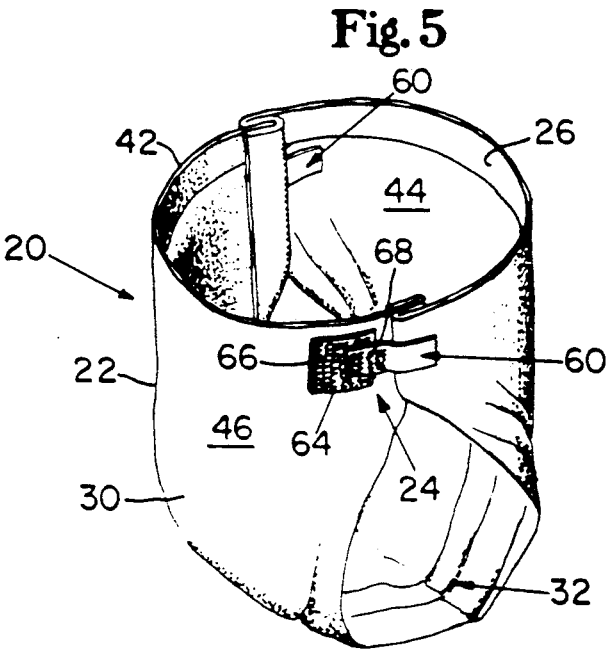
FIG. 5 is a perspective view showing the diaper of FIG. 1 in the configuration it would assume when placed on a wearer.

The preferred embodiment of the diaper 20 illustrated in FIGS. 2 and 5 has a disposal means 68 that is a separate element comprising a second fastening element 106 joined to at least one of the tape tabs 60. The disposal means 68 preferably comprises a second fastening element 106 affixed to the backing surface 72 of each of the tape tabs 60. While the second fastening material 106 of the disposal means 68 may be positioned on the fastening surface 70 of the tape tab 60, the disposal means 68 is preferably positioned on the backing surface 72 to allow the first fastening element 62 of the opposite tape tab 60 to be conveniently secured to the second fastening element 106 of the disposal means 68 to provide easy closure of the tape tabs 60 for disposal. The second fastening element 106 is also preferably positioned on the connective portion 78 and adjacent the distal edge 71 of the tape tab 60.

The second fastening element 106 of the disposal means 68 may comprise any of the second fastening elements described for use as the landing member 64 of the present invention. For example, the second fastening element 106 of the disposal means 68 may be a unitary element or a separate element, may comprise a number of fastening materials such as a hook fastening material or a loop fastening material, and may be either an identical complementary element or a distinct complementary element. Preferably, the second fastening element 106 of the disposal means 68 is the same material as the second fastening element 66 of the landing member 64 and preferably comprises a loop fastening material engageable with the hook fastening material 84 disposed on the fastening surface 70 of the tape tab 60. Thus, the hook fastening material 84 of one of the tape tabs 60 may be secured to the loop fastening material of the disposal means 68 disposed on the backing surface 72 of the other tape tab 60 to allow the diaper 20 to be secured in a configuration for disposal. The second fastening element 106 of the disposal means 68 is preferably affixed to the backing surface 72 by an adhesive attachment means 108 such as is known in the art, preferably a pressure-sensitive adhesive.

Figure 6:
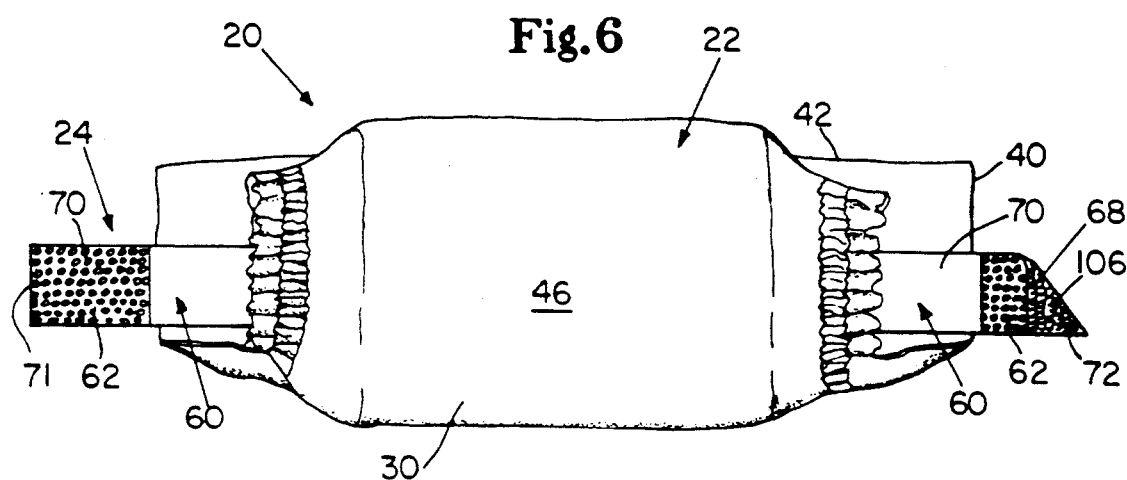
FIG. 6 is a perspective view showing the diaper of FIG. 1 in a configuration for disposal prior to use of the present invention.
Figure 7:
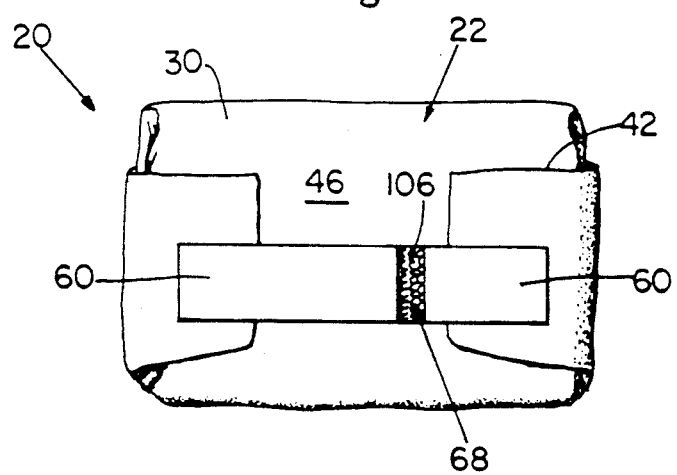
FIG. 7 is a perspective view showing the diaper of FIG. 1 in its disposal configuration with the present invention providing securement of the diaper in the disposal configuration.

In use, the diaper 20 is applied to the wearer by positioning the first end region 48 under the wearer's back and drawing the remainder of the diaper 20 between the legs of the wearer so that the second end region 50 is positioned across the front of the wearer. The connective portion 78 of the tape tabs 60 are then positioned adjacent to the landing members 64 positioned on the outside surface 46 of the second end region 50 so that the first fastening element 62 which is disposed on the fastening surface 70 of the tape tab 60 will engage the second fastening element 66 of the landing member 64 to form a side closure. After the diaper 20 has been soiled, the diaper 20 is removed from the wearer. The diaper 20 is then folded or rolled up into a configuration for disposal. In rolling up the diaper 20, the panels 51 in the second end region 50 are preferably in-folded, and the body portion 22, beginning with the second end region 50, is rolled into a structure such as shown in FIG. 6, with the tape tabs 60 extending outwardly from the rolled-up diaper 20. As shown in FIG. 7, the first fastening element 62 of one of the tape tabs 60 is then secured to the second fastening element 106 of the disposal means 68 disposed on the other tape tab 60 so as to secure the diaper 20 in its rolled-up configuration so that it may be easily and conveniently disposed in a waste receptacle.

Figure 3:
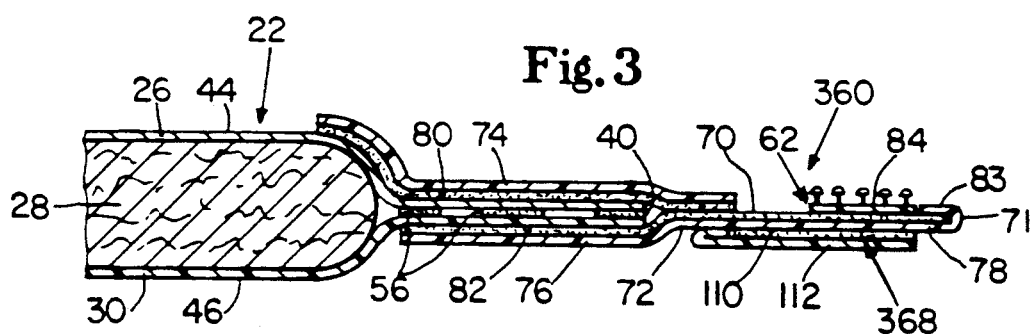
FIG. 3 is a cross-sectional view similar to FIG. 2 of an alternative embodiment of the present invention.

FIG. 3 shows an alternative embodiment of the present invention wherein the disposal means 368 comprises an adhesive attachment means 110 positioned on the tape tab 360, preferably on the backing surface 72 of the tape tab 360, although it may alternatively be positioned on a portion of the fastening surface 70. The disposal means 368 also preferably comprises a release liner 112 positioned on the adhesive attachment means 110 so that the adhesive will not be exposed for use until after the diaper has been soiled. The adhesive attachment means 110 may comprise any adhesive or glue used in the art for such purposes with pressure-sensitive adhesives being preferred. The release liner 112 serves to keep the adhesive attachment means 110 from drying out and from sticking to extraneous surfaces prior to use. Any release liner commonly used for such purposes can be used with this invention. Examples of suitable release liners are BL 30MG-A SILOX E1-0 and BL 30MG-A SILOX 4P/O manufactured by Akrosil Corporation. In this alternative embodiment, after the diaper has been soiled and configured for disposal, the release liner 112 is removed from the adhesive attachment means 110 and the adhesive attachment means 110 are secured either to the other tape tab 360 or to the body portion 22 such as the backsheet 30 so as to secure the diaper in its disposal configuration.

Figure 4:
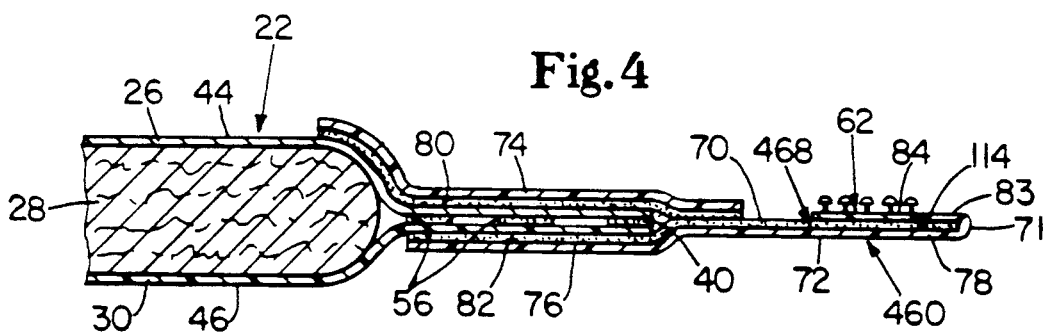
FIG. 4 is a cross-sectional view similar to FIG. 2 of a further alternative embodiment of the present invention.

FIG. 4 shows a further alternative embodiment of the present invention wherein the disposal means 468 comprises an adhesive attachment means 114 (second tab attachment means 82 in this particular embodiment) positioned on the fastening surface 70 of the tape tab 460. The first fastening element 62 of the tape tab 60 is releasably secured to the fastening surface 70 by the adhesive attachment means 114. Since the first fastening element 62 is releasably secured to the fastening surface 70 by the adhesive attachment means 114, after the diaper has been soiled and configured for disposal, the first fastening element 62 is peeled away from the adhesive attachment means 114 and either removed from the tape tab 460 or positioned away from the adhesive to expose the adhesive attachment means 114. The exposed adhesive is used to secure the diaper in its disposal configuration by securing the adhesive attachment means 114 to the other tape tab 460, to the backsheet 30, or to any other portion of the diaper. The adhesive attachment means 114 thus may comprise any of the known adhesives used for such purposes, with pressure-sensitive adhesives being preferred.

FIG. 8 shows another alternative embodiment of the present invention wherein the disposal means 868 comprises an adhesive tape tab 116 positioned on the body portion 22 of the diaper. The adhesive tape tab 116 may comprise any of the adhesive tape tabs as are known in the art. An exemplary adhesive tape tab 116 is described in the above-referenced U.S. Pat. No. 3,848,594. While the adhesive tape tab 116 may be positioned anywhere on the body portion 22 of the diaper, the adhesive tape tab 116 is preferably disposed in the first end region 48, preferably adjacent the end edge 42 of the diaper, and most preferably transversely centered along the end edge 42, to provide a disposal means 868. Thus, when the diaper is folded or rolled up after soiling, the user releases the adhesive tape tab 116 from its release liner and secures the adhesive positioned on the tape tab 116 preferably to the backsheet 30 or another portion of the body portion 22 to provide secure closure of the rolled-up diaper.

FIG. 9 shows a still further alternative embodiment of the present invention wherein the disposal means 968 comprises two adhesive tape tabs 118 and 120, respectively. While the adhesive tape tabs 118 and 120 may be positioned anywhere on the body portion 22 such as adjacent each end edge 42, the adhesive tape tabs 118 and 120 are preferably positioned one adjacent each longitudinal edge of the diaper, more preferably in the first end region 48, and most preferably adjacent the tape tab 60. Thus, in this embodiment, the disposal means 968 comprises a separate set of tape tabs that are to be used either both during wear as a member of the fastening system and after the diaper has been soiled as a disposal means or only after the diaper has been soiled as a disposal means. The adhesive tape tabs 118 and 120 are used as a disposal means 968 by attaching the adhesive disposed on the fastening surface either to the body portion 22 of the diaper such as the backsheet 30 or to each other so as to maintain the diaper in its disposal configuration.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a longitudinal centerline and a lateral centerline, the absorbent article comprising:

a body portion having an inside surface, an opposed outside surface, a pair of longitudinal edges, a pair of end edges, said inside surface and said outside surface extending from one longitudinal edge to the other longitudinal edge, a first end region extending from one end edge of said body portion toward said lateral centerline, and a second end region extending from the other end edge toward said lateral centerline, said body portion comprising a liquid pervious topsheet, a liquid impervious backsheet joined with said topsheet, and an absorbent core disposed between said topsheet and said backsheet, said topsheet forming at least a portion of said inside surface; and a refastenable mechanical fastening system positioned on said body portion, said mechanical fastening system comprising a tape tab disposed adjacent each longitudinal edge of said body portion in said first end region, each of said tape tabs having a fastening surface and a backing surface and comprising a first mechanical fastening means for mechanically engaging complementary elements to form a closure for the absorbent article, said first mechanical fastening means comprising a first fastening element joined on at least a portion of said fastening surface, said first fastening element having elements capable of mechanically engaging complementary elements;

at least one landing member disposed on said outside surface in said second end region, said landing member comprising a second mechanical fastening means for mechanically engaging said first mechanical fastening means to form the closure for the absorbent article, said second mechanical fastening means comprising a second fastening element having elements complementary thereto and mechanically engageable with said elements of said first fastening element so that said second fastening element mechanically engages said first fastening element; and disposal means associated with at least one of said tape tabs for allowing the absorbent article to be secured in a configuration that provides convenient disposal of the absorbent article, means comprising an adhesive attachment means positioned subjacent said first fastening element for releasably adhering said first fastening element to said fastening surface such that said first fastening element may be peeled therefrom when the absorbent article has been soiled to expose said adhesive attachment means and for adhesively securing the absorbent article in a configuration that provides convenient disposal of the absorbent article upon exposure.

2. The absorbent article of claim 1 wherein said disposal means are disposed on each of said tape tabs.

3. A disposable absorbent article having a longitudinal centerline and a lateral centerline, the absorbent article comprising:

a body portion having an inside surface, an opposed outside surface, a pair of longitudinal edges, a pair of end edges, said inside surface and said outside surface extending from one longitudinal edge to the other longitudinal edge, a first end region extending from one end edge of said body portion toward said lateral centerline, and a second end region extending from the other end edge toward said lateral centerline, said body portion comprising a liquid pervious topsheet, a liquid impervious backsheet joined with said topsheet, and an absorbent core disposed between said topsheet and said backsheet, said topsheet forming at least a portion of said inside surface; and a refastenable mechanical fastening system positioned on said body portion, said mechanical fastening system comprising a closure member disposed adjacent each longitudinal edge of said body portion in said first end region, each of said closure members comprising a first mechanical fastening means for mechanically engaging complementary elements to form a closure for the absorbent article, said first mechanical fastening means comprising a first fastening element having elements capable of mechanically engaging complementary elements;

at least one landing member disposed on said outside surface in said second end region, said landing member comprising a second mechanical fastening means for mechanically engaging said first mechanical fastening means to form the closure for the absorbent article, said second mechanical fastening means comprising a second fastening element having elements complementary thereto and mechanically engageable with said elements of said first fastening element so that said second fastening element mechanically engages said first fastening element; and disposal means associated with at least one of said closure members for allowing the absorbent article to be secured in a configuration that provides convenient disposal of the absorbent article, said disposal means comprising an adhesive attachment means positioned subjacent said first fastening element for releasably adhering said first fastening element to said body portion such that said first fastening element may be peeled therefrom when the absorbent article has been soiled to expose said adhesive attachment means and for adhesively securing the absorbent article in a configuration that provides convenient disposal of the absorbent article upon exposure.

4. The absorbent article of claim 3 wherein said closure member comprises an inner fastening member.

5. The absorbent article of claims 1, 3, or 4 wherein said first fastening elements and said second fastening elements are distinct complementary elements.

6. The absorbent article of claim 5 wherein said first fastening element comprises a hook fastening material and said second fastening element comprises a loop fastening material.

7. A method for securing a disposable absorbent article in a configuration for disposal, said method comprising the steps of:

providing a disposable absorbent article having a lateral centerline, said absorbent article comprising (a) a body portion, said body portion having an inside surface, an opposed outside surface, a pair of longitudinal edges, a pair of end edges, a first end region extending from one end edge of said body portion toward said lateral centerline, and a second end region extending from the other end edge toward said lateral centerline, said body portion comprising a liquid pervious topsheet, a liquid impervious backsheet joined with said topsheet, and an absorbent core positioned between said topsheet and said backsheet, said topsheet forming at least a portion of said inside surface, and (b) a refastenable mechanical fastening system comprising (i) a closure member comprising a first mechanical fastening means for forming a closure for the absorbent article, said first mechanical fastening means comprising a first fastening element, said first fastening element having elements capable of mechanically engaging complementary elements, (ii) a landing member comprising a second mechanical fastening means for mechanically engaging said first mechanical fastening means to form the closure for the absorbent article, said second mechanical fastening means comprising a second fastening element having elements complementary thereto and mechanically engageable with said elements of said first fastening element, and (iii) disposal means for allowing the absorbent article to be secured in a configuration that provides convenient disposal of the absorbent article, said disposal means comprising an adhesive attachment means positioned subjacent said first fastening element for releasably adhering said first fastening element to said closure member such that said first fastening element may be peeled therefrom when the absorbent article has been soiled to expose said adhesive attachment means and for adhesively securing the absorbent article in a configuration that provides convenient disposal of the absorbent article upon exposure;

configuring said disposable absorbent article for disposal;

peeling said first fastening element away from said adhesive attachment means so as to expose said adhesive attachment means positioned subjacent said first fastening element; and securing said adhesive attachment means to said body portion of said disposable absorbent article to secure the absorbent article in the configuration for disposal.

8. A method for securing a disposable absorbent article in a configuration for disposal, said method comprising the steps of:

providing a disposable absorbent article having a lateral centerline, said absorbent article comprising (a) a body portion, said body portion having an inside surface, an opposed outside surface, a pair of longitudinal edges, a pair of end edges, a first end region extending from one end edge of said body portion toward said lateral centerline, and a second end region extending from the other end edge toward said lateral centerline, said body portion comprising a liquid pervious topsheet, a liquid impervious backsheet joined with said topsheet, and an absorbent core positioned between said topsheet and said backsheet, at least a portion of said topsheet forming said inside surface, and (b) a refastenable mechanical fastening system comprising (i) a tape tab disposed adjacent each longitudinal edge of said body portion, each of said tape tabs having a fastening surface and a backing surface and comprising a first mechanical fastening means for forming a closure for the absorbent article, said first mechanical fastening means comprising a first fastening element joined on at least a portion of said fastening surface, said first fastening element having elements capable of mechanically engaging complementary elements, (ii) a landing member comprising a second mechanical fastening means for mechanically engaging said first mechanical fastening means to form the closure for the absorbent article, said second mechanical fastening means comprising a second fastening element having elements complementary thereto and mechanically engageable with said elements of said first fastening element, and (iii) disposal means for allowing the absorbent article to be secured in a configuration that provides convenient disposal of the absorbent article, said disposal means comprising an adhesive attachment means positioned subjacent said first fastening element of at least one of said tape tabs for releasably adhering said first fastening element to said fastening surface such that said first fastening element may be peeled therefrom when the absorbent article has been soiled to expose said adhesive attachment means and for adhesively securing the absorbent article in a configuration that provides convenient disposal of the absorbent article upon exposure;

configuring said disposable absorbent article for disposal;

peeling said first fastening element away from said adhesive attachment means so as to expose said adhesive attachment means positioned subjacent said first fastening element; and securing the adhesive attachment means positioned on one of said tape tabs to said body portion or the other tape tab to secure the absorbent article in the configuration for disposal.

9. The method of claim 8 wherein the absorbent article additionally comprises panels in said second end region; and wherein the step of configuring the absorbent article for disposal comprises (i) infolding the panels of said second end region, and (ii) rolling said absorbent article into its disposal configuration with said tape tabs extending outwardly from the rolled-up absorbent article.

* * * * *

UNITED STATES PATENT AND TRADEMARK OFFICE
CERTIFICATE OF CORRECTION

PATENT NO. : 5,279,604
DATED : January 18, 1994
INVENTOR(S) : ANTHONY J. ROBERTSON, et al.

It is certified that error appears in the above-indentified patent and that said Letters Patent is hereby corrected as shown below:

Cover Page, U.S. Patent Documents, "4,585,450 4/1956" should read --4,585,450 4/1985--.

Column 1, line 41, "easilly" should read --easily--.

Column 1, line 59, "sytems" should read --systems--.

Column 3, line 42, "wearere" should read --wearer--.

Column 3, line 44, "to e" should read --to be--.

Column 4, line 7, "flaps 34" should read --flaps 34,--.

Column 4, line 33, "shown in" should read --shown is--.

Column 5, line 25, "material." should read --material).--.

Column 5, line 53, "filament" should read --filaments--.

Column 6, line 19, "the topsheet" should read --The topsheet--.

Column 8, line 25, "U.S. continuation patent applica-" should read --U.S. Continuation Patent Applica---.

Column 9, line 15, "portion 72" should read --portion 74--.

Column 10, line 23, "sue" should read --use--.

Column 10, lines 49 & 50, "patent application" should read --Patent Application--.

Column 11, line 16, ""Scotchmate"" should read --"SCOTCHMATE"--.

UNITED STATES PATENT AND TRADEMARK OFFICE
CERTIFICATE OF CORRECTION

PATENT NO. : 5,279,604
DATED : January 18, 1994
INVENTOR(S) : ANTHONY J. ROBERTSON, et al.

It is certified that error appears in the above-indentified patent and that said Letters Patent is hereby corrected as shown below:

Column 11, line 22, "patent application" should read --Patent Application--.

Column 11, line 67, "4,322.875" should read --4,322,875--.

Column 12, line 28, ""Scotchmate"" should read --"SCOTCHMATE"--.

Column 12, line 41, "patent application" should read --Patent Application--.

Column 16, line 24, "thereto" should read --to--.

Column 16, line 31, "article, means" should read --article, said disposal means--.

Column 16, line 36, "peeled therefrom" should read --peeled and removed therefrom--.

Column 17, line 13, "thereto" should read --to--.

Column 17, line 25, "peeled there-" should read --peeled and removed there---.

Column 18, line 1, "thereto" should read --to--.

UNITED STATES PATENT AND TRADEMARK OFFICE
CERTIFICATE OF CORRECTION

PATENT NO. : 5,279,604
DATED : January 18, 1994
INVENTOR(S) : Anthony J. Robertson, et al It is certified that error appears in the above-indentified patent and that said Letters Patent is hereby corrected as shown below:

Column 18, line 11, "peeled therefrom" should read --peeled and removed therefrom--.

Column 18, line 18, "peeling said" should read --peeling and removing said--.

Column 18, line 59, "thereto" should read --to--.

Column 19, line 2, before "therefrom" insert --and removed--.

Column 19, line 9, "peeling said" should read --peeling and removing said--.

Signed and Sealed this

Twelfth Day of November, 1996

BRUCE LEHMAN

*Attest:*

*Attesting Officer*     *Commissioner of Patents and Trademarks*